(12) United States Patent
Van Roosbroeck et al.

(10) Patent No.: US 12,178,400 B2
(45) Date of Patent: Dec. 31, 2024

(54) METHODS AND SYSTEMS FOR SHAPE SENSING

(71) Applicants: FBGS TECHNOLOGIES GMBH, Jena (DE); FBGS INTERNATIONAL NV, Geel (BE)

(72) Inventors: Jan Van Roosbroeck, Hulshout (BE); Johan Vlekken, Diepenbeek (BE); Bram Van Hoe, Gentbrugge (BE); Christian Voigtlander, Jena (DE); Eric Lindner, Jena (DE)

(73) Assignees: FBGS TECHNOLOGIES GMBH, Jena (DE); FBGS INTERNATIONAL NV, Geel (BE)

( * ) Notice: Subject to any disclaimer, the term of this patent is extended or adjusted under 35 U.S.C. 154(b) by 680 days.

(21) Appl. No.: 17/310,903

(22) PCT Filed: Mar. 4, 2020

(86) PCT No.: PCT/EP2020/055692
§ 371 (c)(1),
(2) Date: Aug. 30, 2021

(87) PCT Pub. No.: WO2020/178336
PCT Pub. Date: Sep. 10, 2020

(65) Prior Publication Data
US 2022/0110508 A1    Apr. 14, 2022

(30) Foreign Application Priority Data

Mar. 5, 2019 (EP) ..................................... 19160918
Oct. 11, 2019 (EP) ..................................... 19202614

(51) Int. Cl.
*A61B 1/00* (2006.01)
*A61B 1/005* (2006.01)
(Continued)

(52) U.S. Cl.
CPC ...... *A61B 1/00154* (2013.01); *A61B 1/00165* (2013.01); *G01B 11/24* (2013.01);
(Continued)

(58) Field of Classification Search
CPC ...................... A61B 2034/2061; A61B 5/6852
See application file for complete search history.

(56) References Cited

U.S. PATENT DOCUMENTS

| | | | |
|---|---|---|---|
| 5,641,956 A * | 6/1997 | Vengsarkar | G02B 6/14 250/227.24 |
| 6,256,090 B1 * | 7/2001 | Chen | G01V 1/3835 356/73.1 |

(Continued)

FOREIGN PATENT DOCUMENTS

| | | | |
|---|---|---|---|
| EP | 3037056 A1 * | 6/2016 | ............. A61B 34/20 |
| WO | 0133165 A1 | 5/2001 | |

(Continued)

OTHER PUBLICATIONS

Extended European Search Report from corresponding Application No. EP19202614.4, Jul. 16, 2020.
(Continued)

*Primary Examiner* — Ryan A Lepisto
*Assistant Examiner* — Erin D Chiem
(74) *Attorney, Agent, or Firm* — Workman Nydegger (57) ABSTRACT

A measurement system for assisting in guiding a tubular-shaped medical device in a body includes a multicore fiber for insertion into a tubular-shaped medical device such that a position of the tip of the multicore fiber corresponds with a position near the tip of the tubular medical device. A plurality of Bragg gratings is inscribed in the multicore fiber. The plurality of Bragg gratings is spaced apart from each other and positioned along the length of the multicore fiber. A measurement device for reading out optical signals is
(Continued)

obtained as a function of a total length of a multicore fiber portion inserted in the body. The measurement device is adapted for deriving shape information of the multicore fiber when the multicore fiber is inserted.

15 Claims, 4 Drawing Sheets (51) Int. Cl.
    *A61B 1/018*     (2006.01)
    *A61B 1/313*     (2006.01)
    *A61B 5/06*     (2006.01)
    *A61B 34/20*     (2016.01)
    *G01B 11/16*     (2006.01)
    *G01B 11/24*     (2006.01)
    *G02B 6/02*     (2006.01)
    *G02B 6/36*     (2006.01)

(52) U.S. Cl.
    CPC .. *A61B 2034/2061* (2016.02); *G02B 6/02042* (2013.01); *G02B 6/02076* (2013.01); *G02B 6/022* (2013.01); *G02B 6/3624* (2013.01)

(56) References Cited

U.S. PATENT DOCUMENTS

| | | | | |
|---|---|---|---|---|
| 6,389,187 | B1* | 5/2002 | Greenaway | G01M 11/083 385/13 |
| 6,888,623 | B2* | 5/2005 | Clements | G01D 5/35341 356/73.1 |
| 7,720,322 | B2* | 5/2010 | Prisco | A61B 34/35 385/12 |
| 7,813,599 | B2 | 10/2010 | Moore | |
| 8,265,431 | B2* | 9/2012 | Childers | E21B 47/007 385/12 |
| 8,610,882 | B2* | 12/2013 | Roberts | G01B 11/165 356/34 |
| 8,746,076 | B2* | 6/2014 | Rogge | G01L 1/24 385/12 |
| 9,429,696 | B2* | 8/2016 | Donhowe | A61B 34/30 |
| 9,636,040 | B2* | 5/2017 | Duindam | A61B 17/3209 |
| 9,976,880 | B2* | 5/2018 | Brehm | G01D 11/00 |
| 11,324,393 | B2* | 5/2022 | Froggatt | A61B 1/00167 |
| 2008/0285909 | A1* | 11/2008 | Younge | A61B 1/009 385/13 |
| 2017/0265946 | A1* | 9/2017 | Ramachandran | A61B 8/4254 |

FOREIGN PATENT DOCUMENTS

| | | | |
|---|---|---|---|
| WO | 2008131303 A2 | 10/2008 | |
| WO | 2012029013 A1 | 3/2012 | |
| WO | 2013144779 A1 | 10/2013 | |
| WO | 2015049142 A1 | 4/2015 | |
| WO | WO-2016202649 A1 * | 12/2016 | ......... A61B 1/00147 |
| WO | 2018011158 A1 | 1/2018 | |

OTHER PUBLICATIONS

International Search Report and Written Opinion from PCT Application No. PCT/EP2020/055692, Jul. 10, 2020.

* cited by examiner

METHODS AND SYSTEMS FOR SHAPE SENSING

FIELD OF THE INVENTION

The present invention relates to the medical field. More particularly, it relates to methods and systems for sensing the shape of a catheter or endoscope.

BACKGROUND OF THE INVENTION

Where possible during surgery or medical examination, one attempts to use minimal invasive surgery or examination rather than open surgery. The latter is advantageous, since it reduces surgical risks as well as pain and it speeds up recuperation after the medical intervention. When applying minimal invasive surgery or examination, often use is made of a catheter or endoscope, further referred to as tube.

In order to provide information to the surgeon regarding the procedure, the insertion of the tube in the body often is done whilst applying medical imaging, in order to assist the surgeon in the procedure, e.g. in deciding where the tube is currently positioned and what direction the tube needs to go. Different medical imaging techniques are available, but at least some of them suffer from the fact that hazardous radiation of/in the body is required.

For determining a direction to go or a position where the tube is positioned, used could also be made of an optical multicore fiber, since the shape of an optical multicore fiber could be determined based on optical signals stemming therefrom. Nevertheless, accuracy of the determination of the shape and position at present is limited, since side effects such as for example twist, limit accurate shape determination and since suitable methods and systems for obtaining position information still need to be improved.

SUMMARY OF THE INVENTION

It is an object of the present invention to provide accurate methods and systems for determining a shape and/or position of a catheter or endoscope using a multicore fiber with gratings, e.g. fiber Bragg gratings (FBG).

It is an advantage of embodiments of the present invention that accurate positional and shape information regarding a catheter or endoscope can be obtained, based on optical measurements in a multicore fiber.

It is an advantage of embodiments of the present invention that measurements of positional and shape information can be fully based on optical measurements in a multicore fiber, since all necessary information can thus be obtained using a single measurement technique, so that no correlation needs to be found between different measurement techniques.

The object and optionally one or more advantages can be obtained using methods and systems according to embodiments of the present invention.

The present invention relates to a measurement system for assisting in guiding tubular shaped medical device in a body. The measurement system comprises a multicore fiber for insertion into the tubular shaped medical device such that a position of the tip of the multicore fiber corresponds with a position near the tip of the tubular medical device, the multicore fiber comprising a plurality of cores, whereby a plurality of Bragg gratings are inscribed in the multicore fiber, the plurality of Bragg gratings being spaced apart from each other and being positioned along the length of the multicore fiber. The measurement system also comprises a measurement device for reading out optical signals obtained from a plurality of cores of a multicore fiber as function of the total length of the multicore fiber portion that has been inserted in the body when a tubular shaped medical device comprising the multicore fiber is inserted into the body, and the measurement device being adapted for deriving, based thereon, shape information of the multicore fiber for deriving therefrom shape information from the tubular shaped medical device wherein the multicore fiber is inserted.

The measurement device may be adapted for providing, based on the optical signals, information regarding the length of the multicore fiber portion that has been inserted in the body.

The measurement system may comprise an output means for outputting obtained shape and length information, or a combination of obtained shape and length information.

Where in embodiments reference is made to shape information, this may refer to local shape information of the multicore fiber, e.g. information of the bending at the tip such as for example the curvature and/or curvature direction, but may also refer to the three dimensional (3D) shape of part or all of the multicore fiber portion that has been inserted in the body.

The measurement device may be adapted for combining the length of the multicore that has been inserted in the body with the shape information.

Where in embodiments of the present invention reference is made to the tip of the multicore fiber, reference may be made to the portion of the multicore fiber closest to the end position inserted in the body with a length smaller than 16 cm, e.g. smaller than 12 cm, e.g. smaller than 8 cm, e.g. smaller than 6 cm.

In embodiments of the present invention, the measurement system may comprise an optical source for irradiating the multicore fiber.

In embodiments of the present invention, the measurement system may comprise one or more optical detectors for detecting a signal, after interaction with the plurality of Bragg gratings, from the plurality of cores.

The measurement device may comprise a processor for processing the different optical signals and for deriving therefrom the shape and/or position information.

In embodiments of the present invention, the multicore fiber may comprise a central core and a plurality of further cores, positioned outside the centre. It is to be noted that the central core is not strictly required.

Embodiments of the present invention advantageously may be used in bodies wherein the channels monitored are substantially static. For example, embodiments may advantageously be used for providing positional information in blood vessels, since the position of the blood vessels does not change with respect to the body. The catheter may be inserted in a blood vessel.

Another example may be for providing positional information in intestines in the human or animal body, whereby a catheter or endoscope is used for surgery or medical examination. Still another example may be for providing positional information in respiratory tracts, e.g. during intubation.

Where in embodiments of the present invention reference is made to a tubular shaped medical device, reference thus for example may be made to a catheter for cardiovascular applications, to an endoscope, to a gastroscope, to a catheter for intubation in respiratory tracts, etc.

According to embodiments of the present invention, deriving shape information of the multicore fiber may comprise deriving a curvature of a portion of the multicore fiber, e.g. of a tip of the multicore fiber, and/or deriving a direction of the curvature of the portion of the multicore fiber, and/or deriving a three dimensional shape of a portion of the multicore fiber. The direction of the curvature at the location of a grating in the multicore fiber typically may be obtained by determining a bending plane at the position of the grating. A change in the direction of the curvature along the multicore fiber, may be obtained by determining a difference in bending planes between two different gratings in the portion of the multicore fiber, e.g. subsequent gratings along the length of the multicore fiber.

The plurality of Bragg gratings may comprise at least two Bragg gratings positioned in the tip of the multicore fiber and the measurement device may be adapted for deriving shape information based on the optical signals from said gratings in the tip in the multicore fiber.

The measurement device may be adapted for deriving shape and/or position information of the tubular shaped medical device taking into account previous recorded optical signals from said gratings in the tip of the multicore fiber as function of the total length of the multicore fiber portion that has been inserted in the body.

The length information of the multicore that has been inserted in the body may be determined based on optical signals from said plurality of cores of the multicore fiber.

It is an advantage of embodiments of the present invention that shape and/or position information of the tubular shaped medical device is derived taking into account previous recorded optical measurements of the gratings in the tip of the multicore fiber. Previously recorded optical measurements thereby may typically correspond with measurements corresponding to another insertion length of the fiber in the body. It is an advantage of embodiments of the present invention that in the tip of the multicore fiber, significantly less twist occurs compared to other portions of the multicore fiber, so that shape information is not or less influenced by twist of the multicore fiber.

The plurality of Bragg gratings may comprise Bragg gratings positioned along substantially the full length of the multicore fiber. It is an advantage of embodiments of the present invention that optical information from Bragg gratings along the length of the multicore fiber can be used for determining a position of the point of entrance in the body, i.e. to determine the length of the portion of the multicore fiber being inserted in the body.

The measurement device may be adapted for determining, based on the optical signals measured from the multicore fiber, a known shape applied to the multicore fiber, and for deriving based thereon, a length of the portion of the multicore fiber that has been introduced in the body. The known shape may be a predetermined shape at a fixed position from the entry point, applied using a specific application means, further referred to as guiding means, or may be a known shape, e.g. determined by the insertion of the tubular shaped medical device in the body. It is to be noticed that, although such a shape can vary patient by patient and insertion by insertion, its general shape is sufficiently determined so that it can be recognised and used in the methods and systems according to the present invention. The shape may for example have a high curvature, e.g. it may be determined by a position having a highest curvature, or a high curvature, e.g. above a predetermined value or it may be determined by a position having a specific sequence of curvatures. For example, in some embodiments the first high bending applied to the tip of multicore fiber when starting to introduce the fiber in the body may be determining the insertion position.

The measurement system may be configured for tracking the position of the insertion point into the body along the multicore fiber when further inserting the tubular shaped medical device in the body. Although it is possible to have two similar shapes along the path, which in principle would be difficult to distinguish, the system may be configured to first register a reference point corresponding to the location of the predetermined shape along the fiber, and from then on follow the movement of a characteristic of this predetermined shape, e.g. the curvature, to track the insertion length while inserting the catheter. Using this tracking principle, it still will be possible to obtain correct position information, even if two or more similar shapes occur along the path.

It is an advantage of embodiments of the present invention that the length of the portion of the multicore fiber that has been introduced in the body can be determined based on optical signals. The known shape may be a curvature introduced at a position where the catheter or endoscope are inserted in the body—in this case no guiding means is required, although often an inserter is used for introducing e.g. a catheter in the body—or it may be a predetermined curvature applied to the multicore fiber—e.g. to the catheter in which the multicore fiber is provided—by a guiding means positioned at a known distance with respect to the entrance point in the body. In some embodiments the inserter may induce a predetermined shape in the multicore fiber or in the tubular shaped medical device.

The system furthermore may comprise a guiding means for guiding the catheter, said guiding means being positionable at a known distance and orientation with reference to the entrance point of the catheter in the body, the guiding means inducing a known shape to the catheter and the multicore fiber inserted therein and the measurement device being adapted for determining, based on the optical signals measured from the multicore fiber, the position of the known shape on the tubular shaped medical device and for determining the length of the inserted portion of the tubular shaped medical device based thereon.

It is an advantage of particular embodiments of the present invention that the determination of the length of the catheter portion inserted in the body can be determined independent of the longitudinal strain and temperature effects on the fiber as these are common mode effects that do not affect the curvature or shape measurement.

It is an advantage of particular embodiments of the present invention that the determination of the insertion or retraction speed of the tubular shaped medical device in the body can be determined.

The measurement device may be adapted for determining, based on the optical signals, a speed of inserting or retracting of the catheter or endoscope comprising the multicore fiber. It is an advantage of particular embodiments of the present invention that information regarding retracting or inserting of the tubular shaped medical device can be obtained from optical measurements.

The measurement device may be adapted for obtaining information regarding the length of the portion of the multicore fiber inserted in the body based on fitting obtained shape information of the optical fiber.

The measurement device may be adapted for obtaining information regarding the shape of the portion of the multicore fiber inserted in the body based on optical signals obtained during insertion or retraction of the multicore fiber from the Bragg gratings in the tip of the multicore fiber. It is an advantage of embodiments of the present invention that information can be used of measurements obtained only with the Bragg gratings in the tip of the multicore fiber during previous measurements performed in an earlier stage of inserting or retracting in the body the catheter or endoscope comprising the multicore fiber. Previously recorded optical measurements thereby may typically correspond with measurements corresponding to another insertion length of the fiber in the body.

It is an advantage of particular embodiments of the present invention that the determination of the shape of the catheter portion inserted in the body is not limited to the resolution determined by the distance between the plurality of Bragg gratings, but that a better resolution can be obtained due to the use of previously recorded shape information as function of the total length of the multicore fiber portion that has been inserted in the body. Such previously recorded shape information thus are measurements corresponding to different insertion lengths of the catheter portion inserted in the body, but performed preferably within the same insertion/retraction action for the multicore fiber in the body. A single action thereby starts from the moment the catheter enters the body and ends when the catheter is completely retracted from the body.

The shape information of the catheter may include a view of the 3D shape of the tubular shaped medical device with respect to the body.

The output means may be adapted for taking into account referencing of a coordinate system coupled to the multicore fiber with respect to a coordinate system of the body. The reference may be created using a predetermined shape as indicated above.

Referencing may be performed taking into account referencing a 3D coordinate system coupled to the guiding means, with respect to the coordinate system of the body, i.e. thus defining a relation between the guiding means introducing a particular shape and the body. Similarly, referencing may be performed taking into account referencing to a 3D coordinate system coupled to the insertion means for inserting the tubular shaped medical device in the body, with respect to the coordinate system of the body, i.e. thus defining a relation between the inserting means and the thus introduced tubular shaped medical device on the one hand and the body on the other hand.

The measurement device may be adapted for determining a relative orientation of the tip of the tubular shaped medical device with respect to a coordinate system of the object or the body.

The multicore fiber or the tube furthermore may comprise an anti-twisting means positioned at the tip of the multicore fiber for further reducing twist of the tip of the multicore fiber. The anti-twisting means may be a sleeve to fit over the tip of the multicore fiber and/or the tube, the sleeve reducing twisting of the tip of the multicore fiber and/or the tube.

In some embodiments, the measurement system furthermore may comprise a temperature sensor for obtaining temperature information. The measurement device of the measurement system may be adapted for taking into account sensed temperature information.

The multicore fiber may comprise at least 3 outer cores, such as for example 3 or 6 outer cores. These further cores may be distributed evenly around a central core.

In one aspect, the present invention also relates to a method for assisting in guiding a catheter or endoscope in a body, the method comprising
inserting a multicore fiber into a tubular shaped medical device such that a position of the tip of the multicore fiber corresponds with a position near the tip of the tubular shaped medical device,
inserting the tubular shaped medical device into the body, deriving optical signals from a plurality of cores of the multicore fiber as function of the total length of the multicore fiber portion that has been inserted in the body.
and deriving based on these optical signals shape and/or position information of the tubular shaped medical device. The method further may comprise using the shape information for determining the actual length that the multicore fiber has been inserted in the body. The latter can for example be based on comparing the obtained shape information with a particular shape near the entrance position on the body, e.g. caused by the introduction of the medical device in the body or by a predetermined-shape inducing device positioned near the entrance position on the body. The method thus is a method for determining the actual length of insertion of a tubular shaped medical device into a body.

Where reference is made to a measurement "as function of the total length" of the multicore fiber portion that has been inserted in the body, reference is made to a measurement as function of the total length of the multicore fiber portion that has been inserted in the body or a parameter related thereto. Where reference is made to a measurement "along the length" of the multicore fiber that has been inserted in the body, reference is made to a measurement for different longitudinal positions on the multicore fiber portion that has been inserted in the body.

The method further may comprise outputting shape information and/or length information. Further steps may correspond with the functionality of the components of the measurement system as described in the first aspect.

The present invention also relates to a graphical user interface adapted for showing shape and/or positional information of the tubular shaped medical device based on optical signals obtained from a plurality of cores of a multicore fiber as function of the total length of the multicore fiber portion that has been inserted in the body when a tubular shaped medical device comprising the multicore fiber is inserted into the body. The length information may be determined based on optical signals from said plurality of cores of the multicore fiber.

In another aspect, the present invention also relates to a non-transitory computer program product adapted for, when run on a processor, performing the steps of determining shape information and/or positional information of the tubular shaped medical device based on optical signals obtained from a plurality of cores of a multicore fiber as function of the total length of the multicore fiber portion that has been inserted in the body when a tubular shaped medical device comprising the multicore fiber is inserted into the body. The length information also being determined based on optical signals from said plurality of cores of the multicore fiber.

In one aspect, the present invention also relates to a measurement system for assisting in guiding tubular shaped medical device in a body, the measurement system comprises a multicore fiber for insertion into the tubular shaped medical device such that a position of the tip of the multicore fiber corresponds with a position near the tip of the tubular medical device. The measurement device further is adapted for determining, based on the optical signals measured from the multicore fiber, a known shape applied to the multicore fiber, and for deriving based thereon, a length of the portion of the multicore fiber that has been introduced in the body. The known shape may be a predetermined shape, applied using a specific application means, further referred to as guiding means, or may be a known shape, e.g. determined by the insertion of the tubular shaped medical device in the body. It is to be noticed that, although such a shape can vary patient by patient and insertion by insertion, its general shape is sufficiently determined so that it can be recognised and used in the methods and systems according to the present invention. Further features optionally may be added and may correspond with one, a combination or all of the features as described above.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments it is indicated that the position of the tip of the multicore fiber corresponds with a position of the tip near the tubular medical device, it is to be noted that this will typically not be perfectly matching, since the tubular medical device typically may have a specially shaped tip, such as for example an ablation tip, which does not allow to enter the fiber until the end of the tubular shaped medical device. Nevertheless, the fiber may be sufficiently far introduced in the tubular shaped medical device so that it provides relevant information from the tubular shaped medical device, e.g. even from the tip thereof.

Where in embodiments of the present invention reference is made to the fiber comprising a plurality of cores which are used for obtaining information, it will be clear for the person skilled in the art that the number of cores used does not need to be limiting for the total number of cores present in the fiber. In other words, the number of cores present in the fiber may be larger than the number of cores actually used for the measurement. During measuring, the cores used may also be changed, as well as the number of cores that are used. Where in embodiments reference is made to the plurality of cores, reference thus may typically be made to the cores used for measuring, rather than to the total number of cores that is present in the fiber.

In a first aspect, the present invention relates to a measurement system for assisting in guiding tubular shaped medical device in a body. Such a tubular shaped medical device may for example be a catheter for blood vessels, a catheter for intubation, an endoscope, a gastroscope, etc. The system advantageously may be used for obtaining information regarding propagation of the tubular shaped medical device in vessels, tracts or intestines or for obtaining information, e.g. visualising, vessels, tracts or intestines. According to embodiments of the present invention, the measurement system comprises a multicore fiber for insertion into the tubular shaped medical device such that a position of the tip of the multicore fiber corresponds with a position of the tip near the tubular medical device. The multicore fiber comprises a plurality of cores. These cores may be organised as a central core surrounded by a plurality of other cores, although embodiments are not limited thereto. In some embodiments, the multicore fiber may have a central core and 3 or more cores arranged around it, e.g. 3 cores or 6 cores. The cores arranged around the central core, are also called outer cores. In embodiments of the present invention, the number of cores used in the measurement system may be different, i.e. lower, than the number of cores that is actually present in the multicore fiber. Depending on the measurements performed, different cores may be selected for use. For measuring curvature, advantageously cores are used which do not all are positioned in the same plane. According to embodiments of the present invention, in the multicore fiber, a plurality of Bragg gratings are inscribed. The plurality of Bragg gratings typically are spaced apart from each other and are positioned along the length of the multicore fiber.

According to embodiments of the present invention, the measurement system also comprises a measurement device for reading out optical signals obtained from a plurality of cores of a multicore fiber as function of the total length of the multicore fiber portion that has been inserted in the body when a tubular shaped medical device comprising the multicore fiber is inserted into the body. It is to be noted that also the length information of the portion of the fiber that has been inserted in the body, advantageously is determined based on optical signals from said plurality of cores of the multicore fiber. Based on the above information, the measurement device is furthermore adapted for deriving shape and/or position information of the multicore fiber for deriving therefrom shape and/or position information from the tubular shaped medical device wherein the multicore fiber is inserted. Such shape information may be local shape information, such as curvature and/or a direction of curvature, but also may include more information such as for example a three dimensional shape of a longer portion of the optical multicore fiber, thus representing a three dimensional shape of the tubular shaped medical device or representing a shape of the vessels, tracts or intestines wherein the tubular shaped medical device is positioned. The information also can advantageously be used for guiding the tubular shaped medical device in the body.

The measurement device may comprise one or more optical detectors for reading the optical response of the cores upon interaction of the radiation with the Bragg gratings. Such one or more optical detectors may correspond with conventional optical detectors used when interrogating an optical fiber, and are as such well known to the person skilled in the art. Such optical detectors also may have or provide a spectrometer function, as known to the person skilled in the art.

It will be understood that the system typically may comprise an optical source for irradiating the multicore fiber. The source nevertheless also may be external to the measurement system and radiation may for example alternatively also be introduced using an internal optical source, details of the optical source used will be known to the person skilled in the art, since the principle of optical interrogation of Fiber Bragg gratings is as such known.

In one set of embodiments, the present invention relates to a measurement system as described above, whereby for obtaining shape and/or position information of the multicore fiber, only measurements of gratings of the end portion, also referred to as the tip, of the optical multicore fiber is used. The tip refers to the portion inserted first in the body. An advantage of such embodiments is that this portion typically is less subject to twist and therefore, the change in curvature direction determined in this way, is substantially more representative of the change in bending direction of the tubular shaped medical device. For determining the curvature as such, a single grating is typically sufficient, whereas for determining the change in curvature direction of the vessel, tract or intestines, typically two gratings, e.g. neighbouring gratings, may be used. The change in curvature direction of the vessel, tract or intestines may typically be determined based on the difference in bending planes for two neighbouring gratings, for example the two gratings positioned closest to the end point or for example the last but one and second last but one gratings. By recording the information as function of a given insertion length of the portion of the multicore fiber that is inserted in the body, accurate shape and/or position information along the length of the multicore fiber can be determined. By systematically recording shape information for the tip over time during the insertion of the tubular shaped medical device, i.e. for different insertion lengths, the full shape of the medical device that has been inserted in the body can be mapped, and thus also of the vessel, tract or intestines can be determined. In these type of measurements, use thus is made of shape information that is previously recorded, within the same insertion or retraction action, but at an earlier moment in time during the insertion or retraction which corresponds to another position of the catheter in the body. Previously recorded optical measurements thereby may typically correspond with measurements corresponding to another insertion length of the fiber in the body.

Basically, a recording is made of the shape information from the tip of the fiber as function of the total length of the portion of the tubular shaped medical device that is inserted in the body. Based on this recording, the shape and/or position information along the length of the multicore fiber that has been inserted in the body can be determined.

Formulated differently, as the shape of the vessel, tract or intestines does not change at a position corresponding with a certain length of insertion of the tubular shaped medical device (due to the fact that the vessels, tracts or intestines do not change shape or position during the measurement procedure), the shape information recorded from the tip of the fiber at different moments in time, i.e. for different insertion lengths, translates into shape information along the length of the inserted tubular shaped medical device that is inserted in the body.

An advantage of using previous data recorded during the same insertion or retraction event is that the resolution of the information obtained, e.g. shape information, is not limited by the interdistance between the gratings along the fiber but can be higher depending on how accurate the insertion length of the multicore fiber in the body can be determined and the speed of insertion and the time interval between the measurements that are performed. These can be selected so that the resolution with which the information is captured can be higher than based on the interdistance between the gratings on the fiber. By fitting the curvature profile at the pre-defined shape position, one can thus even determine the insertion length at a sub FBG spacing resolution, i.e. the resolution higher than the one determined by the spacing between the fiber gratings.

In alternative embodiments, the shape information is gathered using more gratings than only those at the tip of the optical multicore fiber, and/or the shape information is combined with length information which is also determined using optical measurements of the multicore fiber.

According to embodiments of the present invention, length information regarding the portion of the optical multicore fiber that is inserted in the body can be obtained based on detection of a particular shape or curvature induced in the optical multicore fiber at a known position with respect to the entry position of the optical multicore fiber in the body or the entry point of the tubular shaped medical device comprising the optical multicore fiber. Two examples of how such a particular shape or curvature can be obtained are described below. Nevertheless, in other embodiments the length information may be determined based on a different principle, such as for example based on a mechanical measurement, e.g. using a kapstan, or for example based on optical imaging, e.g. using a camera, or for example based on the information of a catheter drive system of a robotic based catheterization system, etc.

Figure 1:
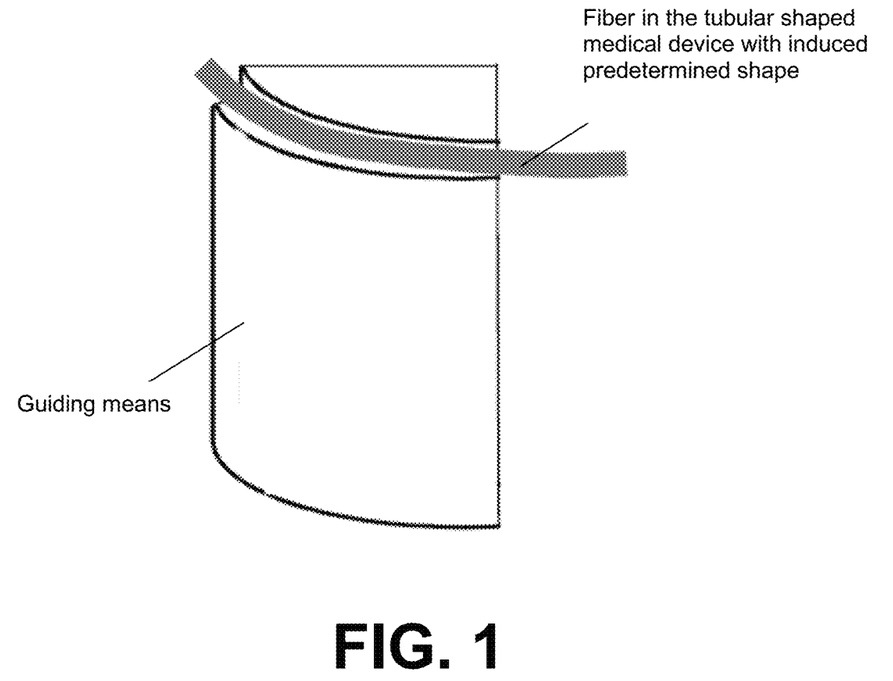
FIG. 1 illustrates a guiding means as can be used in a measurement system according to an embodiment of the present invention.

In a first example, the measurement system comprises a guiding means through which the tubular shaped medical device is guided, wherein the guiding means has a known position with respect to the entry point of the tubular shaped medical device into the body. The guiding means furthermore is adapted for inducing in the tubular shaped medical device, a particular shape or curvature such as for example a partial circular shape. By way of illustration, embodiments not being limited thereto, an example of such a guiding means inducing a circular shape is shown in FIG. 1 and FIG. 4.

Figure 4:
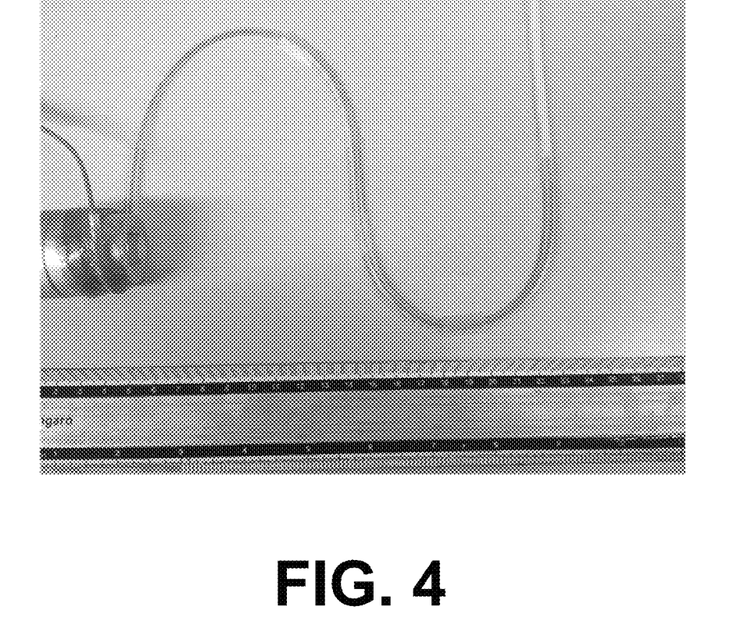
FIG. 4 illustrate an experimental set-up containing a multicore fiber in a catheter sleeve for illustrating features of a measurement system according to an embodiment of the present invention. At the left side on this figure, a guiding means consisting of a Teflon tube bended over a metal cylinder with a radius of 1.6 cm is applied. The guiding means goes over into a sine shaped Teflon tube which represents a blood vessel. The catheter sleeve containing the optical fiber is inserted from the left side passing first the guiding means after which it enters the vessel phantom. On the figure, the catheter sleeve and multicore fiber are inserted over one period of the sine wave.
Figure 5:
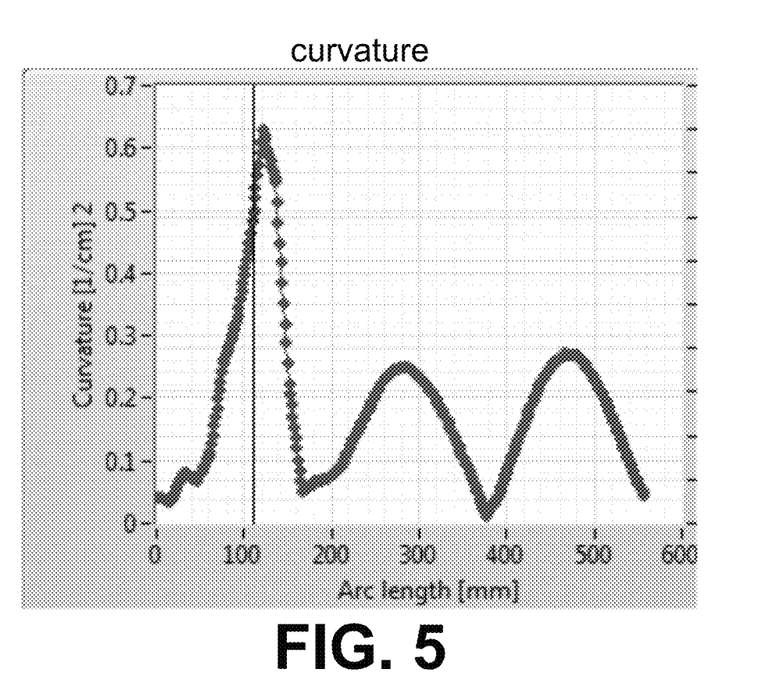
FIG. 5 to FIG. 6 illustrate measurements of an experiment for illustrating features of a measurement system according to an embodiment of the present invention.

In FIG. 4, the guiding means imposes a bending to the multicore fiber with a radius of 1.6 cm, which corresponds to a curvature of 0.625 (1/cm). FIG. 5 shows the curvature measured along the multicore fiber. As can be seen, a curvature of about 0.625 (1/cm) can be seen at a fiber length position of 120 mm, which can be determined as the position where the guiding means applies the biggest curvature to the fiber.

It is an advantage of embodiments of the present invention that the guiding means is not only used as reference for the position but also as a reference for the orientation of the fiber in space, as the orientation of the fiber at the position where the guiding means induces the particular curvature is also known. The latter may allow to create a reference frame wherein both the position as well as the orientation of the fiber is known.

Figure 2:
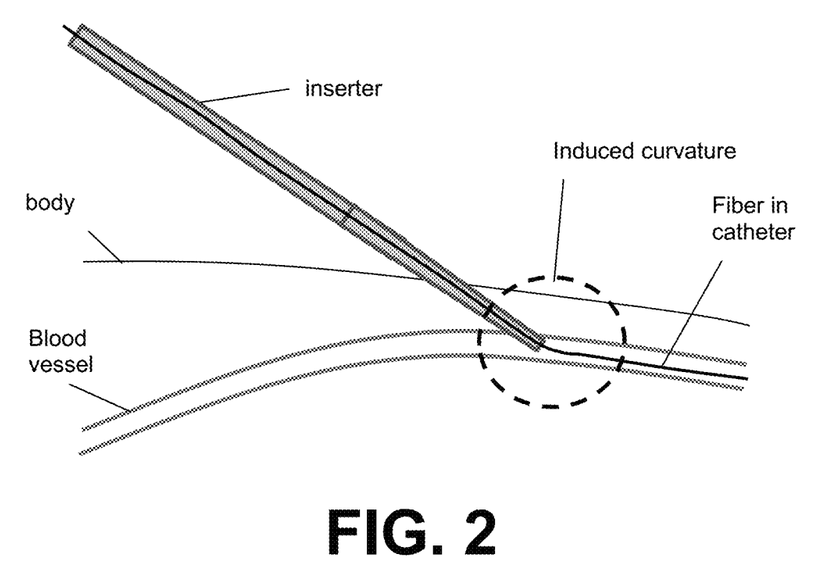
FIG. 2 illustrates induced curvature due to insertion of a catheter in the body, as can be used in an embodiment according to the present invention.

In a second example, the measurement system does not provide a guiding means inducing a particular shape in the tubular shaped medical device, but the particular shape in the tubular shaped medical device is induced by the way the tubular shaped medical device is inserted in the body. The latter is illustrated in FIG. 2, where an inserter is used for inserting the tubular shaped medical device in the body, and wherein a specific curvature is illustrated.

Independent of the particular technique used, the detection of the position on the fiber that fulfils the particular shape (curvature) can be used to identify a reference point with respect to the point of insertion of the tubular shaped medical device, and as a consequence provides information regarding the length of the portion of the tubular shaped medical device that has been inserted in the body with a resolution better than the interdistance between the gratings along the fiber. The particular shape (curvature) of the reference point thus induces a fingerprint at the position of the multicore fiber that at that moment is located at the reference point. The position of this fingerprint along the length of the multicore fiber can be detected using shape information obtained from the different gratings along the length of the optical multicore fiber, e.g. curvature information measured at the different sensor positions In some embodiments, very accurate insertion length can be obtained by fitting or interpolating the measured shape information at the position of the reference point, e.g. fitting the curvature information at the reference point to the particular shape. By fitting or interpolating the measured shape information, the insertion length can be determined with a higher resolution than the interdistance between the gratings. (i.e. high accuracy).

According to embodiments of the present invention, shape and/or position of the tubular shaped medical device is obtained from shape information obtained from gratings in the tip of the fiber as function of the total length of the multicore fiber portion that has been inserted in the body.

Figure 6:
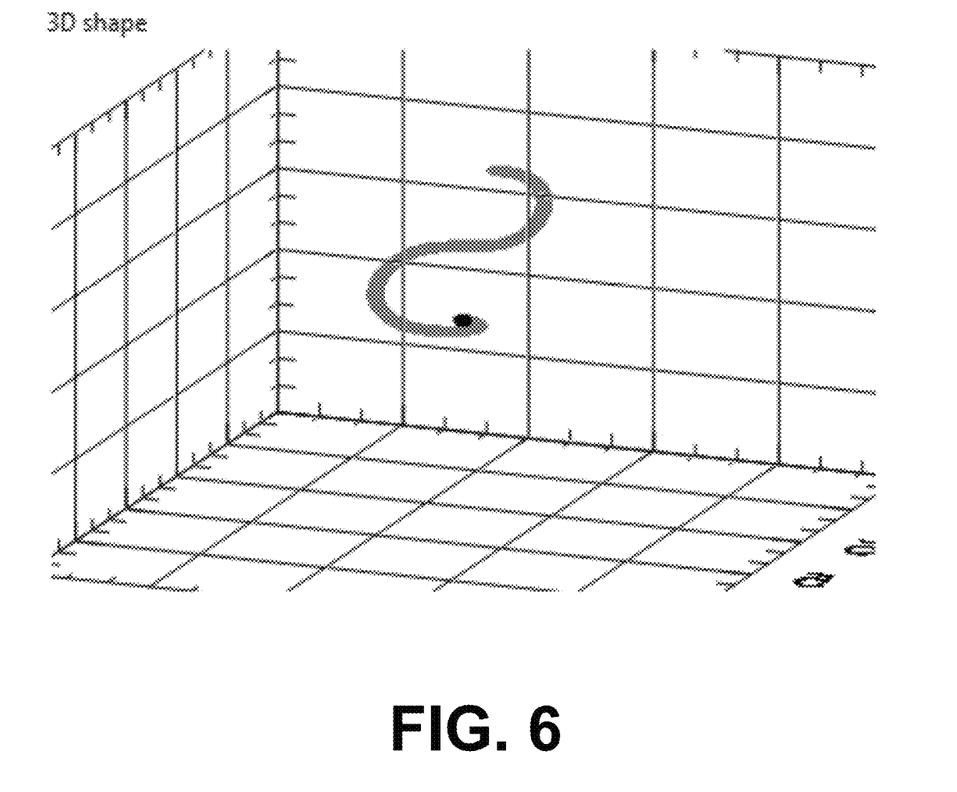

The latter is illustrated in FIG. 4 to FIG. 6.

Figure 7:
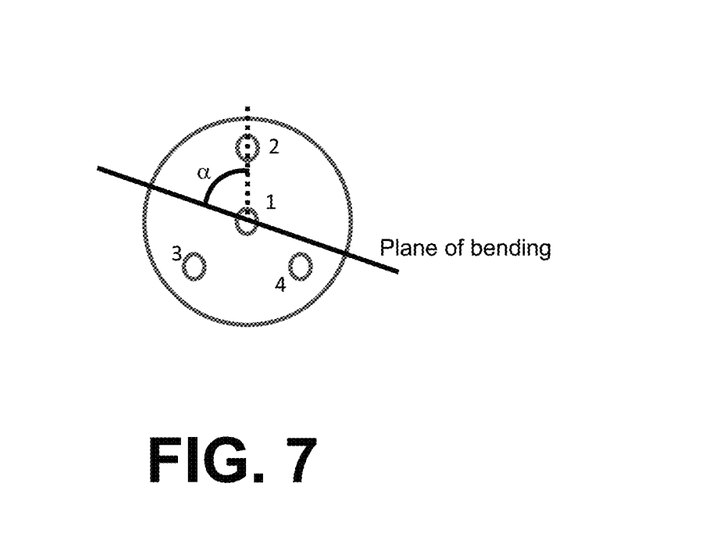
FIG. 7 illustrates schematically the orientation of the bending plane of a multicore fiber with respect to an outer core, as used in embodiments of the present invention.

FIG. 7 illustrates a schematic overview of a cross section of the fiber that is used for the experiment. The multicore fiber used is a 4 core fiber, whereby a single core is positioned centrally and wherein 3 cores are distributed evenly around the central core. For the results shown, all three outer cores, cores 2, 3 and 4 were monitored. The fiber has a 125 μm cladding and a 200 μm Ormocer-T coating, comprising 38 gratings with length of 4 mm and with a spacing of 1.5 cm, resulting in a total sensing length of 555 mm. The fiber is cut after sensor 38.

FIG. 4 illustrates a simulation of a catheter inside a blood vessel after passing a known shape. At the left of the figure, a guiding means consisting of a Teflon tube bended over a metal cylinder with a radius of 1.6 cm, which corresponds to a curvature of 0.625 (1/cm). The guiding means goes over into a sine shaped Teflon tube which represents a blood vessel. The catheter sleeve containing the optical fiber has a total length of about 650 mm with a sensing length of about 555 mm and is inserted from the left side passing first the guiding means after which it enters the vessel. The catheter sleeve and multicore fiber are inserted over one period of the sine wave.

FIG. 5 shows the related curvature profile measured along the multicore fiber corresponding with the fiber inserted in the phantom vessel as shown in FIG. 4. The curvature profile in the first 160 mm illustrate here the curvature occurring at the known shape near the entrance of the blood vessel and is used as a reference point for determining length information regarding the portion that has been introduced in the blood vessel. As can be seen, a curvature of about 0.625 (1/cm) can be seen at a fiber length position of 120 mm, which corresponds to the position where the guiding means applies the biggest curvature to the multicore fiber. Based on this position, the inserted portion of the fiber in the body can be calculated as the total fiber length is well known. As a consequence the shape information from the tip of the fiber can be allocated to a certain position in the body.

By recording this shape information for different inserted fiber lengths in the body, the 3D shape of the path of the catheter sleeve can be reconstructed like is shown in FIG. 6. FIG. 6 shows the calculated 3D shape for the fiber corresponding to the fiber like it was inserted in FIG. 4. The small bending at the beginning of the curve shows the position of the bending means. Furthermore, the shape shows also one period of the sine wave over which the catheter sleeve containing the multicore fiber is inserted in the vessel.

According to some embodiments, the present invention also can be adapted for determining a speed of insertion or retraction of the tubular shaped medical device as the insertion length of the multicore fiber in the body can be determined as function of time. The latter may be useful for training as well as medical reporting reasons.

By way of illustration, embodiments of the present invention not being limited thereto, the principle of how to derive a bending radius, or a curvature, and bending orientation is discussed for a particular example below. Whereas the situation is discussed using a particular mathematical formalism, it is to be understood that embodiments are not limited thereto and that this is only provided for illustrating the principle. A possible principle of determining the final 3D shape or position information of a multicore fiber based on these curvatures and bending orientations is also disclosed for example in U.S. Pat. No. 7,813,599, and thus considered to be known as such for the person skilled in the art. According to the present invention however, the 3D shape information is calculated based on the shape information recorded from the tip of the multicore fiber as function of the total length of the multicore fiber portion that is inserted in the body.

The bending radius and direction can be derived from a shift in wavelengths of different outer gratings located at a sensor position along the fiber. The FBG wavelength shift $\Delta\lambda$ in the different cores has several contributions: (1) bending strain, (2) fiber twist, (3) longitudinal strain and (4) temperature changes. The bending strain can be calculated from the bending radius R and the distance of the core with the central plane of bending: strain=distance from plane/bending radius. The distance between the core and the bending plane can be expressed in terms of the distance d between the central core and the eccentric core together with the angle that the core makes with the central plane of bending. The distance d equals 38 µm for the used fiber in the current example but of course will depend on the fiber used, the example not being limiting for embodiments of the present invention. The angle with the central bending plane can be expressed in terms of the angle $\alpha$, which is defined as the angle between core 2 and the central plane of bending. A schematic view is shown in FIG. 7.

Let $\Delta\varepsilon_{twist}$ be the strain originating from the fiber twist, $\Delta\varepsilon_{long}$ the longitudinal strain component and $\Delta T$ the change in temperature, then the total wavelength shift $\Delta\lambda$ in each core can be expressed as follows:

$$\begin{cases} \Delta\lambda_2 = \left(\frac{d.\sin\alpha}{R} + \Delta\varepsilon_{twist} + \Delta\varepsilon_{long}\right).s_\varepsilon + \Delta T.s_T \\ \Delta\lambda_1 = (\Delta\varepsilon_{long}).s_\varepsilon + \Delta T.s_T \\ \Delta\lambda_3 = \left(\frac{d.\sin(\alpha+120°)}{R} + \Delta\varepsilon_{twist} + \Delta\varepsilon_{long}\right).s_\varepsilon + \Delta T.s_T \\ \Delta\lambda_4 = \left(\frac{d.\sin(\alpha+240°)}{R} + \Delta\varepsilon_{twist} + \Delta\varepsilon_{long}\right).s_\varepsilon + \Delta T.s_T \end{cases}$$

with $s_\varepsilon$ and $s_T$ the strain respectively temperature sensitivity. This gives us 4 equations and 5 unknowns. It is clear that we can solve it for 4 independent parameters: R, $\alpha$, $\Delta\varepsilon_{twist}$ and ($\Delta\varepsilon_{long}\cdot s_\varepsilon + \Delta T \cdot s_T$). The solution can be found based on the following goniometric relations:

$$\begin{cases} \sin(\alpha+120°) = \sin(\alpha).\cos(120°) + \cos(\alpha).\sin(120°) \\ = \sin(\alpha).\cos(180°-60°) + \cos(\alpha).\sin(180°-60°) \\ = -\sin(\alpha).\cos(60°) + \cos(\alpha)\sin(60°) \\ = -\frac{1}{2}\sin(\alpha) + \frac{\sqrt{3}}{2}\cos(\alpha) \end{cases}$$

$$\begin{cases} \sin(\alpha+240°) = \sin(\alpha-120°) \\ = \sin(\alpha).\cos(120°) - \cos(\alpha).\sin(120°) \\ = \sin(\alpha).\cos(180°-60°) - \cos(\alpha).\sin(180°-60°) \\ = -\sin(\alpha).\cos(60°) - \cos(\alpha)\sin(60°) \\ = -\frac{1}{2}\sin(\alpha) - \frac{\sqrt{3}}{2}\cos(\alpha) \end{cases}$$

With these expressions, a solution can be found:

$$\begin{cases} tg\alpha = -\frac{\sqrt{3}}{3} \cdot \left(\frac{2\Delta\lambda_2 - \Delta\lambda_3 - \Delta\lambda_4}{\Delta\lambda_4 - \Delta\lambda_3}\right) \\ R = \frac{\sqrt{3}\, d.s_\varepsilon}{(\Delta\lambda_3 - \Delta\lambda_4)}\cos\alpha \\ \Delta\varepsilon_{twist} = \left[\frac{1}{3}(\Delta\lambda_2 + \Delta\lambda_3 + \Delta\lambda_4) - \Delta\lambda_1\right]/s_\varepsilon \\ \Delta\varepsilon_{long}.s_\varepsilon + \Delta T.s_T = \Delta\lambda_1 \end{cases}$$

Figure 3:
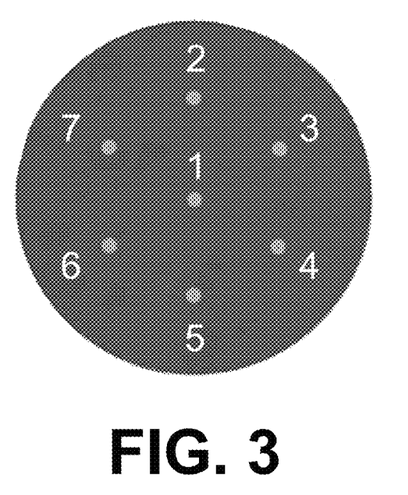
FIG. 3 illustrates the cross section of a multicore fiber containing 1 center and 6 outer cores.

In case we have a 7-core fiber, it can sometimes be useful to use a combination of 3 other cores, not necessarily under angles of 120°. Consider for example the case of 3 adjacent outer cores, each at 60° such as for example core 2, 3 and 4 in FIG. 3.

In principle, this configuration contains the same information compared to the 120° configuration since the bending strain of the core 3 is similar in size (but opposite in sign) than the opposite core, core 6. In this case, we end up with the following set of equations:

$$\begin{cases} \Delta\lambda_2 = \left(\frac{d.\sin\alpha}{R} + \Delta\varepsilon_{twist} + \Delta\varepsilon_{long}\right).s_\varepsilon + \Delta T.s_T \\ \Delta\lambda_3 = \left(\frac{d.\sin(\alpha+60°)}{R} + \Delta\varepsilon_{twist} + \Delta\varepsilon_{long}\right).s_\varepsilon + \Delta T.s_T \\ \Delta\lambda_4 = \left(\frac{d.\sin(\alpha+120°)}{R} + \Delta\varepsilon_{twist} + \Delta\varepsilon_{long}\right).s_\varepsilon + \Delta T.s_T \end{cases}$$

For finding the solution, we can make use of the following goniometric equation:

$$\sin(\alpha+60°) = \frac{1}{2}\sin(\alpha) + \frac{\sqrt{3}}{2}\cos(\alpha)$$

A solution can be found in a similar way like for the more symmetric case. After some math, the following solution can be found:

$$\begin{cases} tg\alpha = \sqrt{3}.\left(\frac{\Delta\lambda_3 - \Delta\lambda_4}{3\Delta\lambda_3 - \Delta\lambda_4 - 2\Delta\lambda_2}\right) \\ R = \frac{d.s_\varepsilon}{(\Delta\lambda_3 - \Delta\lambda_4)}\sin\alpha \end{cases}$$

The above provides an illustration on how the bending radius and bending direction can be derived, and it will be understood that it is only given by way of illustration.

The present invention advantageously combines shape sensing with length information regarding the length of the multicore fiber that is inserted in the body. It allows in some embodiments to use only shape information determined based on grating positioned at the tip of the fiber, while using another technique for determining the insertion length. A major advantage of at least some embodiments of the present invention lies in the fact that the relative change in the bending plane measured between neighbouring gratings positioned at the tip of the multicore fiber is almost identical to the change in curvature direction of the fiber at that position in the body, since in these embodiments the effect of for example twist can be neglected. By using, in some embodiments, previously recorded data of the gratings in the tip in combination with corresponding previously recorded length measurements of the portion of multicore fiber that is inserted in the body, shape information such as three dimensional shape and/or position information of the fiber can be obtained substantially independent of twist in the multicore optical fiber. Previously recorded optical measurements thereby may typically correspond with measurements corresponding to another insertion length of the fiber in the body. It thus is noted that whereas the curvature measurement as such always provides the proper results, the change in bending plane is not always a correct representation of the change in the bending direction of the multicore fiber as it can also be affected by twist of the fiber. By reducing twist, determination of the change in bending plane provides more direct information regarding the change in bending direction of the fiber.

It also allows in some embodiments to obtain very accurate three dimensional shape and/or position information, whereby such information is obtained by combining the shape information measured from gratings positioned at the tip as function of the total length of the multicore fiber portion that has been inserted in the body, with the momentary shape information measured using a plurality of gratings positioned along the length of the multicore fiber.

In some embodiments, this may result in two independent measurements for obtaining shape information so that cross-checking can be performed. In other embodiments, the three dimensional shape and/or position information can be obtained, for example by deriving the curvature along the length of the multicore fiber, which is a measurement that is not influenced by the twist, using the momentary shape information measured using a plurality of gratings positioned along the length of the multicore fiber, while deriving the bend direction from the measurements of the gratings positioned at the tip as function of the total length of the multicore fiber portion that has been inserted in the body. By combining these measurements, the three dimensional shape and/or position information of the multicore fiber can also be determined.

In a second aspect, the present invention relates to a method for assisting in guiding a tubular shaped medical device in a body. The body may be a human or animal body, or may be a dead object. The method comprises inserting a multicore fiber into a tubular shaped medical device such that a position of the tip of the multicore fiber corresponds with a position of the tip near the tubular shaped medical device, inserting the tubular shaped medical device into the body, deriving optical signals from a plurality of cores of the multicore fiber as function of the total length of the multicore fiber portion that has been inserted in the body and deriving based on these optical signals shape information along the tubular shaped medical device that has been inserted into the body. The method also may comprise outputting shape information and/or position information. Further steps may correspond with the functionality of the components of the measurement system as described in the first aspect and therefore are not repeated here.

In a further aspect, the present invention relates to a graphical user interface adapted for showing shape information of the tubular shaped medical device, based on optical signals obtained from a plurality of cores of a multicore fiber as function of the total length of the multicore fiber portion that has been inserted in the body when a tubular shaped medical device comprising the multicore fiber is inserted into the body, the length information also being determined based on optical signals from said plurality of cores of the multicore fiber. Such a graphical user interface thus advantageously may be coupled to a measurement system according to the first aspect, showing the information obtained therewith. The graphical user interface may show local shape information of the optical multicore fiber, such as for example of the tip of the multicore fiber. It may be used for guiding the tubular shaped medical device in the body. Advantageously, the graphical user interface can provide orientation information of the multicore fiber with respect to a 3D coordinate system coupled to the body. It can for example take into account the orientation with respect to the body when displaying the position information of the multicore optical fiber. The graphical user interface may display other information as obtainable with a system according to the first aspect.

In yet another aspect, the present invention also relates to a non-transitory computer program product adapted for, when run on a processor, performing the steps of determining shape information of the tubular shaped medical device, based on optical signals obtained from a plurality of cores of a multicore fiber as function of the total length of the multicore fiber portion that has been inserted in the body when a tubular shaped medical device comprising the multicore fiber is inserted into the body the length information also being determined based on optical signals from said plurality of cores of the multicore fiber. The non-transitory computer program product may furthermore be adapted for, when executed on a computer, performing methods steps corresponding with the functionality of components of the measurement system according to the first aspect.

In still another aspect, the present invention relates to a comparted catheter for use in a method according to the second aspect of the present invention. The comparted catheter advantageously has a central compartment, so that the optical multicore fiber can be inserted in such central compartment, such that it can be optimally used for determining shape information regarding the catheter. One example of such a catheter may be a catheter with a central compartment and with additionally one or more compartments positioned near the side of the catheter. The present invention also relates to the use of comparted catheter for obtaining shape information according to a method of a second aspect of the present invention.

The invention claimed is:

1. A measurement system for assisting in guiding a tubular-shaped medical device in a body, the measurement system comprising:
    a multicore fiber for insertion into a tubular shaped medical device such that a position of a tip of the multicore fiber corresponds with a position near the tip of the tubular shaped medical device, the multicore fiber comprising a plurality of cores, whereby a plurality of Bragg gratings are inscribed in the multicore fiber, the plurality of Bragg gratings being spaced apart from each other and being positioned along a length of the multicore fiber, and
    a measurement device for:
        reading out optical signals obtained of the plurality of cores of the multicore fiber as function of total length of a multicore fiber portion that has been inserted in the body when the tubular shaped medical device comprising the multicore fiber is inserted into the body, and
        deriving, based thereon, shape information of the multicore fiber and for deriving therefrom shape information from the tubular shaped medical device wherein the multicore fiber is inserted,
    wherein deriving shape information comprises obtaining a difference in bending planes between two different subsequent Bragg gratings along the length in the tip of the multicore fiber and using previously recorded optical measurements of the plurality of Bragg gratings.

2. The measurement system according to claim 1, wherein the plurality of Bragg gratings comprises at least two Bragg gratings positioned in the tip of the multicore fiber and wherein the shape information is derived based on the optical signals from said gratings in the tip in the multicore fiber.

3. The measurement system according to claim 1, wherein the length information of the portion of the multicore fiber inserted in the body is being determined based on optical signals from the plurality of cores of the multicore fiber.

4. The measurement system according to claim 1, wherein the plurality of Bragg gratings comprises Bragg gratings positioned along substantially a full length of the multicore fiber.

5. The measurement system according to claim 1, wherein the measurement device is adapted for determining, based on the optical signals measured from the multicore fiber, a known shape applied to the multicore fiber, and for deriving based thereon, a length of the portion of the multicore fiber that has been introduced in the body.

6. The measurement system according to claim 5, wherein the system furthermore comprises a guiding means for guiding the tubular shaped medical device, said guiding means being positionable at a known distance with reference to an entrance point of a catheter in the body, the guiding means inducing a known shape to the tubular shaped medical device and the multicore fiber inserted therein and the measurement device being adapted for determining, based on the optical signals measured from the multicore fiber, the position of the known shape on the tubular shaped medical device and for determining the length of the inserted portion of the tubular shaped medical device based thereon.

7. The measurement system according to claim 6, wherein the shape information of the tubular shaped medical device includes a view of a 3D shape of the tubular shaped medical device with respect to the guiding means or with respect to a known shape.

8. The measurement system according to claim 1, wherein the measurement device is adapted for obtaining information regarding the length of the portion of the multicore fiber inserted in the body based on fitting obtained shape information of the optical fiber at a location of a known shape.

9. The measurement system according to claim 1, wherein the measurement device is adapted for obtaining information regarding the shape of the portion of the multicore fiber inserted in the body based on optical signals obtained during insertion or retraction of the multicore fiber from the Bragg gratings in the tip of the multicore fiber.

10. The measurement system according to claim 1, wherein the measurement system furthermore comprises an output means adapted for outputting shape information taking into account referencing of a coordinate system coupled to the multicore fiber with respect to a coordinate system of the body.

11. The measurement system according to claim 1, wherein the measurement device is adapted for determining a relative orientation of the tip of a tubular shaped medical device with respect to a coordinate system of the body.

12. The measurement system according to claim 1, wherein the measurement device is adapted for determining, based on the optical signals, a speed of inserting or retracting of the tubular shaped medical device comprising the multicore fiber.

13. The measurement system according to claim 1, wherein the multicore fiber and/or the tubular shaped medical device furthermore comprises an anti-twisting means positioned at the tip of the multicore fiber and/or at the tip of the tubular shaped medical device for further reducing twist of the tip of the multicore fiber.

14. A graphical user interface adapted for, using the measurement system according to claim 1, showing shape information based on optical signals obtained from a plurality of cores of a multicore fiber as function of the total length of the multicore fiber portion that has been inserted into a body when a tubular shaped medical device comprising the multicore fiber is inserted into the body.

15. A non-transitory computer program product adapted for, using the measurement system according to claim 1, when run on a processor, performing the steps of determining shape information based on optical signals obtained from a plurality of cores of a multicore fiber as function of the total length of the multicore fiber portion that has been inserted into a body when a tubular shaped medical device comprising the multicore fiber is inserted into the body.

* * * * *